United States Patent

Geuder

[11] Patent Number: 5,879,356
[45] Date of Patent: Mar. 9, 1999

[54] SURGICAL INSTRUMENT FOR CRUSHING CRYSTALLINE EYE LENSES BY MEANS OF ULTRASOUND AND FOR REMOVING LENS DEBRIS BY SUCTION

[75] Inventor: Volker Geuder, Heidelberg, Germany

[73] Assignee: Hans Geuder GmbH, Heidelberg, Germany

[21] Appl. No.: 874,765

[22] Filed: Jun. 13, 1997

[30] Foreign Application Priority Data

Jan. 13, 1997 [DE] Germany ............... 197 00 809.7

[51] Int. Cl.⁶ ............................................. A61F 9/00
[52] U.S. Cl. ................... 606/107; 604/22; 604/51
[58] Field of Search ..................... 606/107, 128; 604/22, 51

[56] References Cited

U.S. PATENT DOCUMENTS 5,354,265 10/1994 Mackool ............................ 604/22

FOREIGN PATENT DOCUMENTS 40 08 594  9/1991  Germany .
WO 96/25883  8/1996  WIPO .

OTHER PUBLICATIONS

Cataract/IOL Enclosed (p. 11) Publication of Hans Geuder GmbH. Enclosed.

Primary Examiner—Michael Buiz
Assistant Examiner—Julian W. Woo
Attorney, Agent, or Firm—Collard & Roe, P.C.

[57] ABSTRACT

A surgical instrument is intended for use in cataract operations, and includes an ultrasonic probe in the form of a hollow needle which is connected with a suction conduit, through which lens debris is removed by suction together with a rinsing liquid. The rinsing liquid is supplied to the site of surgery via a flow path extending between the hollow needle and a sleeve surrounding this needle with a spacing from the needle. This sleeve extends approximately along the entire length of the hollow needle and has at its distal end at least one outlet aperture for the rinsing liquid. The sleeve has two layers, in which an outer jacket layer is made of tissue compatible plastic such as silicone. A small inner tube layer is positioned and fitted within the outer jacket. This inner tube is made of a material having greater stiffness than the material of the outer jacket, and radially supports the outer jacket.

4 Claims, 2 Drawing Sheets

५,८७९,३५६

SURGICAL INSTRUMENT FOR CRUSHING CRYSTALLINE EYE LENSES BY MEANS OF ULTRASOUND AND FOR REMOVING LENS DEBRIS BY SUCTION

BACKGROUND OF THE INVENTION

1. Field of the Invention

The present invention relates to a surgical instrument for crushing crystalline eye lenses by means of ultrasound, and for removing the lens debris by suction. A hollow needle is connected with an ultrasound generator received in a handpiece. The lumen of the needle is communicatively connected in terms of flow with a suction duct extending through the handpiece. The needle is surrounded by a sleeve made of plastic, forming a flow path communicatively connected in terms of flow with a feed duct of the handpiece for feeding rinsing liquid. This sleeve extends approximately along the entire length of the hollow needle, and has near its front end at least one outlet aperture for the rinsing liquid.

2. The Prior Art

Instruments useful for eye surgery are described in DE 40 08 594 A. Publications of Hans Geuder GmbH of Hertzstrasse 4, Heidelberg, Germany, relate to these instruments also.

In connection with such instruments, a needle forming an ultrasonic probe extends axially from a handpiece and is detachably screwed into a needle receptacle. This receptacle is designed like a sleeve and is longitudinally movable within the handpiece at high frequency, in a known manner.

The needle is a hollow needle with a lumen for removing by suction the rinsing liquid, and the lens debris carried along by this liquid. The lumen is connected with a suction conduit through a duct extending through the handpiece. The rinsing liquid is fed through a ring duct surrounding the end of the needle receptacle that is screwed onto the hollow needle.

When the instrument is used as intended, a plastic cap is exchangeably screwed onto the end of the handpiece at the needle end. This cap receives in a suitably dimensioned chamber, the end of the needle receptacle and a head of the hollow needle screwed to the receptacle. The plastic cap has a sleeve extending from the chamber, and surrounds the needle approximately along its entire length, forming a ring duct which is sealed at the front end of the sleeve, and which has lateral outlet apertures for rinsing liquid.

When the instrument is used, the hollow needle with the sleeve of the plastic cap surrounding it is inserted through an incision at the edge of the cornea into the anterior chamber of the eye which is to undergo the surgery. In a known manner, the lens is crushed by means of the hollow needle forming the ultrasonic probe. This is because the probe, which has a beveled segment at its end in most cases, focuses ultrasound into the lens. Rinsing liquid flows through the ring duct surrounding the needle receptacle, which is longitudinally movable at high frequency. The rinsing liquid then flows into the rear chamber of the plastic cap receiving the front end of the needle receptacle and the head of the needle screwed to the receptacle. Then the rinsing liquid flows via the ring duct between the hollow needle and the sleeve of the plastic cap surrounding the hollow needle. In this manner, rinsing liquid is supplied to the site of the surgery, and is then removed again by suction from the anterior chamber of the eye together with lens debris, via the lumen extending through the hollow needle.

Instruments of this type have been used successfully and, as a rule, permit without any problems the removal of lenses in cataract surgery. This is done by crushing the lens by means of ultrasound into very fine particles, and then by removing these particles by suction together with the rinsing liquid previously admitted into the anterior chamber of the eye. At the same time, the rinsing liquid flowing through the ring duct serves as a thermal insulation of the sleeve against the hollow needle, which heats up highly during the course of an operation.

It has been found that the sleeve, which in most cases consists of flexible material such as silicone, can be easily manipulated within the area of the wound. However, the sleeve may be constricted by the pressure applied by the edges of the wound, until this sleeve comes to rest against the hollow needle. This may lead to local heating of the sleeve, and in extreme cases, it may even lead to strangulation of the ring duct. In connection with this ring duct strangulation, it may lead to overheating of the entire area between the site of the constriction and the needle point. This consequently leads to damage to the surrounding eye tissue caused by heat, and particularly to the edges of the wound enclosing the sleeve.

In order to avoid such damage, a hollow needle has been described in trade publication "CATARACT/IOL", which has radially outwardly projecting longitudinal ribs on which the sleeve surrounding the hollow needle supports itself radially if constrictions occur. With this state of the prior art, it is assured that feed ducts for the rinsing liquid are kept open with a high degree of probability. However, at the site of any constriction, the sleeve is in direct contact with the ribs of the hollow needle. Such contact areas may cause undesirable heat transfer from the hollow needle, which consists of metal, and which consequently has good thermal conductivity, to the sleeve, and to the eye tissue resting against the outside of the sleeve.

SUMMARY OF THE INVENTION

It is an object of the present invention to improve such a surgical instrument to the extent that irrespective of any constriction of the sleeve caused in cataract surgery by the edges of the eye tissue surrounding the incision, that a an unrestricted free flow of the rinsing liquid between the hollow needle and the sleeve surrounding the needle is assured. Furthermore, in case of any constriction of the sleeve, its contact with the hollow needle and thus transfer of heat to surrounding eye tissue is kept to a minimum and is as negligible as possible.

With the eye surgical instrument of the invention, this object is achieved because the sleeve is constructed of two layers and comprises an outer jacket layer made of tissue-compatible and pliant material such as silicone, and has an inner small tube layer received within the outer jacket. This inner tube is made of a material such as polyamide, which is stiffer as compared to the material used for the outer jacket.

Therefore, it is preferred that the outer jacket and the inner tube of the sleeve surround the hollow needle; and that the outer jacket consists of a material that is easy to manipulate particularly within the area of the wound. Thus, the outer jacket will also have an inner supporting shaft in the form of a small stiffening inner tube, which extends approximately along the entire length of the sleeve and provides the sleeve with dimensional strength and stiffness. Thus, when the sleeve is inserted into an incision at the edge of the cornea, this permits an adaptation to the configuration of such an incision. Advantageously this avoids any complete strangulation of the feed path for the rinsing liquid extending between the hollow needle and the sleeve.

According to an embodiment of the invention, the outer jacket forming the sleeve and the small inner tube received in the outer jacket each have a circular cross section. When they are used as intended, they are elliptically deformable, and are formed into an elliptical cross section but do not constrict each other and do not prevent the flow of the rinsing liquid. When using the instrument as intended, such elliptical deformability has been found to be advantageous. This is because even with an elliptical cross section, the flat sides of the ellipse are pressed by the edges of the wound against or almost against the hollow needle. However, large lumina will remain in the longitudinal direction of the incision for feeding rinsing liquid to the site of surgery through these lumina. This assures an adequate supply of rinsing liquid being fed to the site of surgery. In addition, this prevents any noticeable transfer of heat from the hollow needle through the double walled surrounding sleeve. Thus, no notable damage to the edge of the wound can occur within the site of the incision due to the rinsing liquid cooling effect obtained in this way.

According to another embodiment of the invention, the outer jacket of the sleeve tightly surrounds the small inner tube received therein, so as to create tension radially in the outer jacket. Also, the inner tube is radially spaced from the hollow needle.

BRIEF DESCRIPTION OF THE DRAWINGS

Other objects and features of the present invention will become apparent from the following detailed description considered in connection with the accompanying drawing which discloses several embodiments of the present invention. It should be understood, however, that the drawing is designed for the purpose of illustration only and not as a definition of the limits of the invention.

In the drawing, wherein similar reference characters denote similar elements throughout the several views.

DETAILED DESCRIPTION OF PREFERRED EMBODIMENTS

Figure 1:
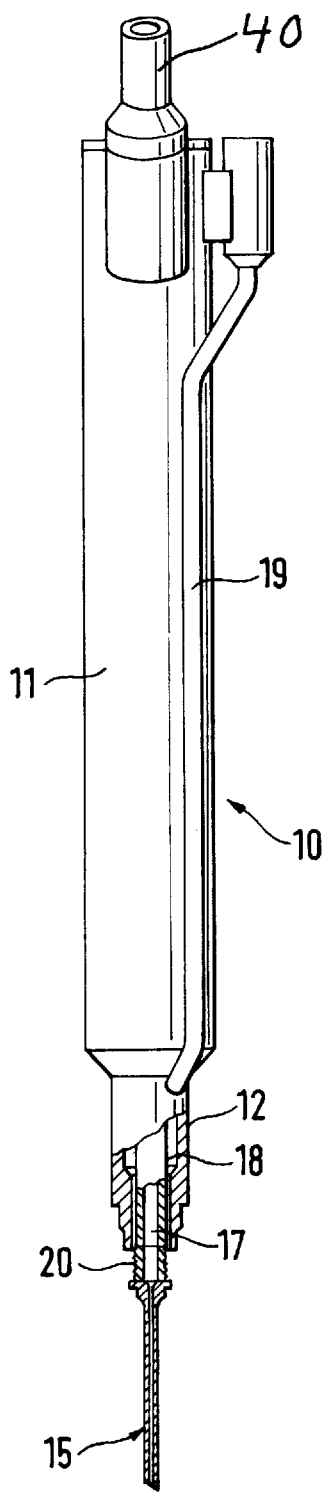
FIG. 1 shows a partial section view of a handpiece with a hollow needle forming an ultrasonic probe, the needle being screwed axially rigidly, but detachably to a needle receptacle, which is longitudinally movable at high frequency.

Turning now in detail to the drawings, FIG. 1 shows the instrument 10 in its totality, and has an elongated handpiece 11 with a needle receptacle 12 guided with longitudinal movability in the handpiece and drivable at high frequency by an ultrasonic generator 43. The needle receptacle 12 exits from the handpiece 11 at the front end of the handpiece and is surrounded by a annular ring duct 13 for feeding rinsing liquid. An ultrasonic probe in the form of a hollow needle 15 is detachably screwed to the front end of the needle receptacle 12. By means of a duct 17 extending through the tappet-like needle receptacle 12, the lumen 16 of this hollow needle is connected with a suction conduit connectable with the other end of the handpiece. Near the front end of the needle receptacle 12, which is connected with the hollow needle 15, is a conduit 19 substantially extending along the entire length of the handpiece 11. Conduit 19 feeds into a chamber 18 concentrically surrounding the needle receptacle 12, with a conduit 19 feeding rinsing liquid into chamber 18 which is connected with the lower end of the conduit 19.

Figure 2:
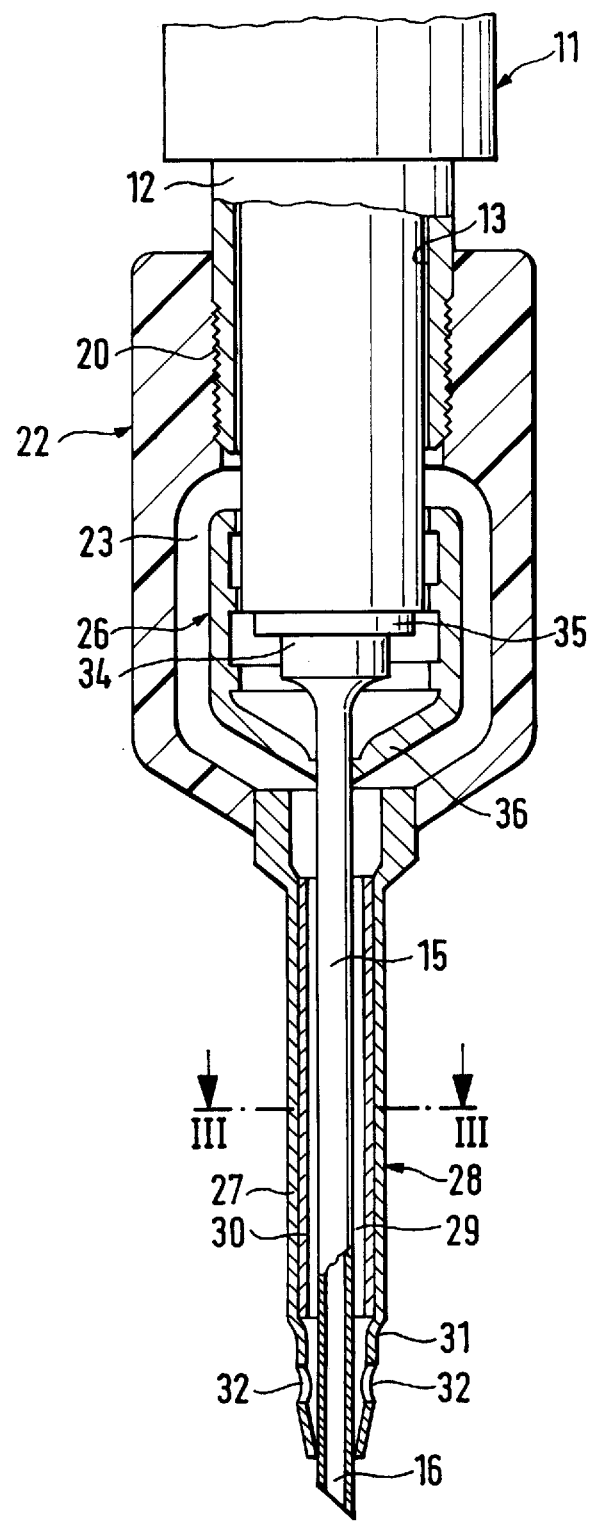
FIG. 2 shows in an enlarged cutout section from FIG. 1, the hollow needle detachably connected with the needle receptacle, and a plastic cap screwed to the end of the handpiece on the needle side, this plastic cap receiving in a chamber the coupling zone between the needle receptacle and the needle, with a sleeve extending from this cap, such sleeve surrounding the hollow needle, forming a ring duct.
Figure 3:
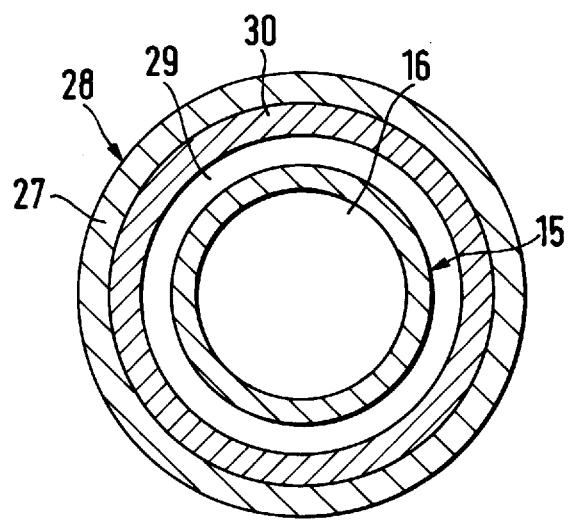
FIG. 3 shows a cross section through the hollow needle and the sleeve surrounding the needle, in accordance with section line III—III in FIG. 2.

The end of handpiece 11 at the needle end is provided with a male thread section 20, to which an exchangeable plastic cap 22 is screwed. This is shown in FIG. 2. The plastic cap 22 has a rear chamber 23, in which an inner sleeve 26 is received. An outer layer jacket 27 of a two-layer sleeve 28 extends from the rear chamber 23 of plastic cap 22. The sleeve 28 surrounds the hollow needle 15 substantially along its entire length, forming an annular or ring duct-shaped flow path 29, as shown in FIG. 3. The outer jacket 27, which consists of a tissue-compatible material such as silicone, accommodates a small inner tube layer 30 made of polyamide. The tube 30 extends along almost the entire length of the outer jacket layer. The small inner tube layer 30 terminates in a cone-like construction 31 of the outer jacket 27 at the distal end of the jacket 27, as shown in FIG. 2. Tube 30 elastically supports the outer jacket 27 in the radial direction, but, when using the instrument as intended, permits deformations of sleeve 28, as described in greater detail below. Within the zone of constriction 31, the outer jacket 27 of sleeve 28 is pierced on opposite sides by two laterally directed outlet apertures 32 for the exiting of the rinsing fluid.

The hollow needle 15 is connected with the needle receptacle 12. The receptacle 12 is longitudinally movable at high frequency, and receptacle 12 has within the connection zone a head 34 with a key attachment piece 35 radially projecting beyond this head. On the side of key attachment piece 35 remote from the actual needle, a threaded pin is screwed into a threaded bore of needle receptacle 12, which is not shown. Head 34 of the needle within the screw joint and key attachment piece 35 adjoining this screw joint, and the face-side end of needle receptacle 12, which has a cylindrical end as shown in FIG. 2, each have a large cross section as compared to the actual cross section of hollow needle 15. These large cross sections act like pistons when longitudinally actuated at a high frequency. Needle head 34 with the key attachment piece 35 and the end of the needle receptacle 12 projecting on the face side beyond the actual handpiece are received within the inner sleeve 26. On the side remote from the needle receptacle 12, the inner sleeve 26 is terminated by a conical bottom 36, through which the actual hollow needle 15 extends in a recess, which is sealed against fluid flow.

With plastic cap 22 screwed to the end of the handpiece 11 at the needle end annular, ring duct 13 for feeding rinsing liquid and surrounding the end of the needle receptacle 12 feeds rinsing liquid into the rear chamber 23 of the plastic cap 22. On the outside of the inner sleeve, flow paths lead radially to the sleeve 28 extending from the chamber 23 on the side facing away from the needle receptacle 12. Thus, a flow path 29 is formed between the small inner tube 30 received in the outer jacket 27 of the sleeve 28, and the hollow needle 15, as shown in FIG. 3. The inner tube 30 radially supports the outer jacket 27.

When the instrument is used as intended, the ultrasonic probe moves longitudinally at a high frequency, and rinsing liquid flows through annular ring duct 13 with ring duct 13 surrounding needle receptacle 12. The rinsing liquid flows into rear chamber 23 of plastic cap 22, and then the rinsing liquid flows around the outer side of inner sleeve 26 enclosing the screw joint between the needle receptacle 12 and the hollow needle 15. The rinsing liquid then flows through flow path 29 between the hollow needle 15 and sleeve 28 with sleeve 28 surrounding the needle 15. With the small inner tube 30 fitted into the outer jacket 27, the rinsing liquid can exit near the distal end of the hollow needle 15 through apertures 32.

Figure 4:
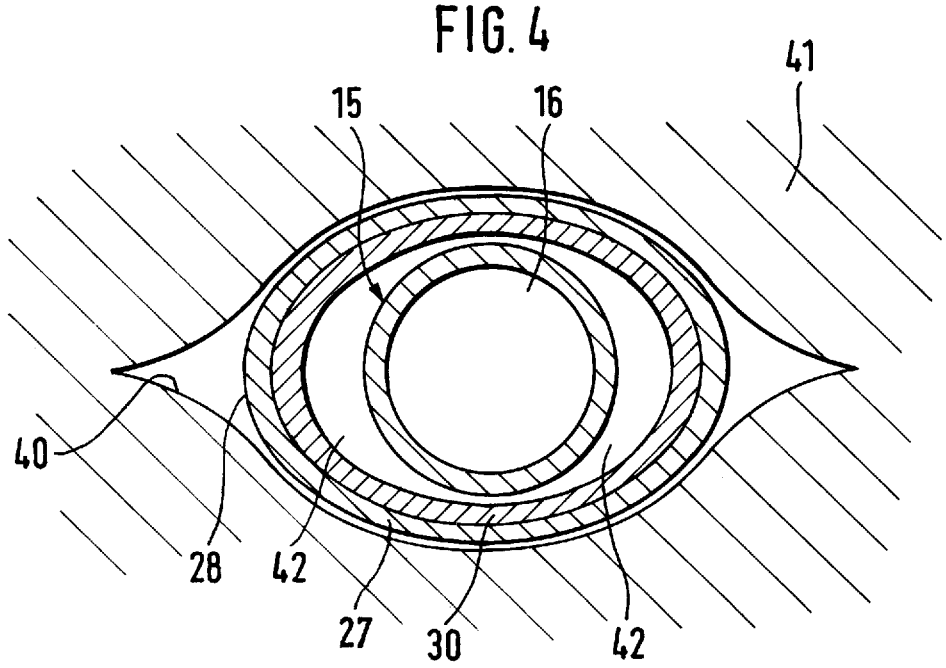
FIG. 4 shows the hollow needle inserted through a cornea incision in the anterior chamber of an eye to undergo surgery, with the sleeve surrounding the hollow needle elliptically deformed and in a section view based on FIG. 3.

The deformation of two-layered sleeve 28 within the area of incision 40 on the edge of cornea 41 (shown shaded) of an eye to be operated on, is shown schematically in FIG. 4. Due to the pressure applied to sleeve 28 by the edges of the wound incision 40, the two-layered sleeve 28 is compressed in a direction transversely to the longitudinal expanse of incision 40 until the small inner tube 30 radially supporting the outer jacket 27 almost comes to rest against the hollow needle 15. Due to the radial support effect of small tube 30 located in the outer jacket 27, the sleeve 28 enclosing the hollow needle 15 concentrically when in the undeformed state, takes on an elliptical shape. As a result of such elliptical deformation as shown in FIG. 4, two moon crescent-shaped flow zones 42 are formed in the longitudinal direction of incision 40 instead of the flow paths 29, as shown in FIG. 3 which are annular ring shaped ducts in the undeformed condition.

The zones 42 assure unobstructed flow of the rinsing liquid to the site of the surgery. It is possible that in a direction perpendicular to the longitudinal expanse of the incision 40, that a pointlike contact or a small amount of contact could be established between hollow needle 15 and the small tube 30 positioned and fitted into the outer jacket 27 of sleeve 28. Even if such contact were to occur, any transfer of heat that could conceivably occur would be reduced in these zones due to the continuous dissipation of heat by the rinsing liquid. This is because of the directly adjacent flow of the rinsing liquid, to an extent such that no damage to the edges of the wound would be caused by this heat.

While several embodiments of the present invention have been shown and described, it is to be understood that many changes and modifications may be made thereunto without departing from the spirit and scope of the invention as defined in the appended claims.

What is claimed is:

1. Ultrasonic surgical instrument for crushing eye crystalline lenses and for removing lens debris comprising a handpiece;

a hollow needle adapted to be connected with an ultrasound generator and received in the handpiece, said hollow needle having a lumen;

the lumen of said needle being communicatively connected for fluid flow with a suction conduit extending through the handpiece;

a sleeve made of plastic surrounding said lumen and communicatively forming a fluid flow path connected with a feed duct of the handpiece for feeding rinsing liquid, said sleeve extending approximately along an entire length of the hollow needle and having near an outlet end at least one outlet aperture for said rinsing liquid;

said sleeve comprising two layers, and one of said two layers being an outer jacket layer made of tissue-compatible and pliant material, and an other of said two layers being a small inner tube layer received within the outer jacket, and said small tube being made of a material which is stiffer than the material of the outer jacket;

wherein the outer jacket layer of the sleeve tightly surrounds a substantial length of the small inner tube layer received within the outer jacket and said inner tube layer radially supports the outer jacket; and wherein said small inner tube layer is radially spaced from the hollow needle.

2. Ultrasonic surgical instrument of claim 1, wherein the outer jacket layer of said sleeve and the small inner tube layer received within said outer jacket, each having a circular cross section and each are deformable into an elliptical cross section when in use, with the proviso that said elliptical cross section does not constrict said fluid flow path.

3. Ultrasonic surgical instrument of claim 1, wherein said outer jacket layer is made of silicone.

4. Ultrasonic surgical instrument of claim 1, wherein said small tube inner layer is made of polyamide.

* * * * *